US009446048B2

(12) United States Patent
Liu et al.

(10) Patent No.: US 9,446,048 B2
(45) Date of Patent: Sep. 20, 2016

(54) METHODS FOR TREATING LEUKEMIA AND DISORDERS MEDIATED BY CBFβ AND RUNX1 PROTEINS

(75) Inventors: Pu Liu, Bethesda, MD (US); Wei Zheng, Potomac, MD (US); Juan Marugan, Gaithersburg, MD (US); Noel T. Southall, Chevy Chase, MD (US); Lea Cunningham, Washington, DC (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 218 days.

(21) Appl. No.: 14/005,534

(22) PCT Filed: Mar. 15, 2012

(86) PCT No.: PCT/US2012/029169
§ 371 (c)(1),
(2), (4) Date: Sep. 16, 2013

(87) PCT Pub. No.: WO2012/125787
PCT Pub. Date: Sep. 20, 2012

(65) Prior Publication Data
US 2014/0004082 A1   Jan. 2, 2014

Related U.S. Application Data

(60) Provisional application No. 61/453,863, filed on Mar. 17, 2011.

(51) Int. Cl.
| *A61K 31/40* | (2006.01) |
| *A61K 31/5513* | (2006.01) |
| *A61K 31/203* | (2006.01) |
| *A61K 31/417* | (2006.01) |
| *A61K 31/704* | (2006.01) |
| *A61K 31/7068* | (2006.01) |
| *A61K 31/7076* | (2006.01) |
| *A61K 45/06* | (2006.01) |
| *A61K 38/20* | (2006.01) |

(52) U.S. Cl.
CPC ......... *A61K 31/5513* (2013.01); *A61K 31/203* (2013.01); *A61K 31/40* (2013.01); *A61K 31/417* (2013.01); *A61K 31/704* (2013.01); *A61K 31/7068* (2013.01); *A61K 31/7076* (2013.01); *A61K 38/2013* (2013.01); *A61K 45/06* (2013.01); *Y10S 514/908* (2013.01)

(58) Field of Classification Search
None
See application file for complete search history.

(56) References Cited

U.S. PATENT DOCUMENTS

| 3,405,122 A | 10/1968 | Berger et al. |
| 5,036,101 A | 7/1991 | Hsu et al. |
| 5,041,438 A | 8/1991 | Hsu |
| 5,141,735 A | 8/1992 | Bellemin et al. |
| 5,164,376 A | 11/1992 | Hsu et al. |
| 5,641,773 A | 6/1997 | Pardee et al. |
| 5,939,430 A | 8/1999 | Tyms et al. |
| 2012/0059003 A1 | 3/2012 | Bushweller et al. |

FOREIGN PATENT DOCUMENTS

| EP | 0 462 522 | 12/1991 |
| WO | WO 2008157407 | 12/2008 |
| WO | WO 2010/120614 | 10/2010 |
| WO | WO 2010132684 | 11/2010 |

OTHER PUBLICATIONS

Kempf et al., Journal of Biomolecular Screening, 2006, vol. 11(7), pp. 807-815.*
Blyth et al., "Runx1 promotes B-cell survival and lymphoma development," *Blood Cells, Molecules, and Diseases* 43:12-19, 2009 (available online Mar. 9, 2009).
Blyth et al., "Runx2 in normal tissues and cancer cells: A developing story," *Blood Cells, Molecules, and Diseases* 45:117-123, 2010.
Egawa et al., "The role of the Runx transcription factors in thymocyte differentiation and in homeostasis of naïve T cells," *Journal of Experimental Medicine* 204(8):1945-1957, Aug. 6, 2007 (available online Jul. 23, 2007).
Gorczynski et al., "Development of an allosteric inhibitor of the protein-protein interaction between RUNX1 and CBF beta," *American Chemical Society* 230:2736, Aug. 1, 2005 (Abstract only).
Hyde et al., "RUNX1 Repression-Independent Mechanisms of Leukeomogenesis by Fusion Genes *CBFB-MYH11* and *AML1-ETO (RUNX1-RUNX1T1)*," *Journal of Cellular Biochemistry* 110:1039-1045, 2010.
Khalid et al, "Modulations of Runx2 activity by Estrogen Receptor α: Implications for Osteoporosis and Breast Cancer," *Endocrinology* 149(12):5984-5895, Dec. 2008 (available online Aug. 28, 2008).
Kira et al., "2-Glycineamide-5-chlorophenyl 2-pyrryl ketone, a non-benzodiazepin Tat antagonist, is effective against acute and chronic HIV-1 infections in vitro," *Antiviral Research* 32:55-62, 1996.
Li et al., "A novel microRNA targeting HDAC5 regulates osteoblast differentiation in mice and contributes to primary osteoporosis in humans," *The Journal of Clinical Investigation* 119(12): 3666-3677, Dec. 2009.
Mendoza-Villanueva et al., "The Runx transcriptional co-activator, CBFβ, is essential for invasion of breast cancer cells," *Molecular Cancer* 9:171, 2010.

(Continued)

*Primary Examiner* — Savitha Rao
*Assistant Examiner* — Gregg Polansky
(74) *Attorney, Agent, or Firm* — Klarquist Sparkman, LLP

(57) ABSTRACT

A method for treating core binding factor (CBF) leukemia in a subject, comprising administering to a subject having CBF leukemia a therapeutically effective amount of a compound, or a pharmaceutically acceptable salt or ester thereof, that inhibits CBFβ and RUNX1 binding in the subject, thereby treating the CBF leukemia.

13 Claims, 10 Drawing Sheets

(56) References Cited

OTHER PUBLICATIONS

Otto et al., "Mutations in the RUNX2 Gene in Patients with Cleidocranial Dysplasia," *Human Mutation* 19:209-216, 2002.

Pratap et al., "Metastatic Bone Disease: Role of transcription factors and future targets," *Bone* 48(1):30-36, 2011 (available online Jun. 1, 2010).

Rudra et al., "Runx-CBFβcomplexes control expression of the transcription factor Foxp3 in regulatory T cells," *Nature Immunology* 10(11):1170-1178, Nov. 2009 (available online Sep. 20, 2009).

Sato et al., "The Distinct Role of the Runx Proteins in Chondrocyte Differentiation and Intervertebral Disc Degeneration," Arthritis & Rheumatism 58(9):2764-2775, Sep. 2008.

Song et al., "Haploinsufficiency of *CBFA2* causes familial thrombocytopenia with propensity to develop acute myelogenous leukaemia," *Nature Genetics* 23:166-175, Oct. 1999.

International Search Report from International Application No. PCT/US2012/029169, dated May 18, 2012.

Written Opinion of the International Searching Authority from International Application No. PCT/US2012/029169, dated May 18, 2012.

PubChem CID 284708, created Mar. 26, 2005.

PubChem CID 64983, created Mar. 26, 2005.

PubChem CID 60859, created Aug. 1, 2005.

Gorczynski et al, "Allosteric Inhibition of the Protein-Protein interaction between the Leukemia-Associated Proteins Runx1 and CBFβ" *Chemistry & Biology*, 14:1186-1197, Oct. 2007.

\* cited by examiner

FIG. 3
High-Throughput Screen for
Inhibitors of RUNX1-CBFβ Interaction
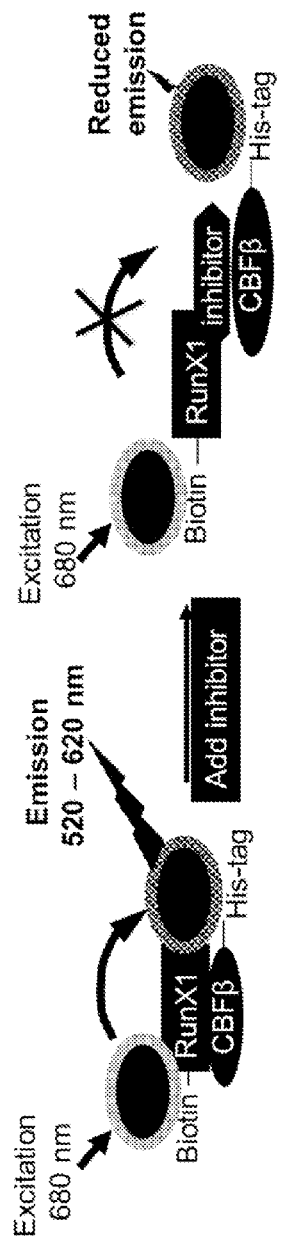
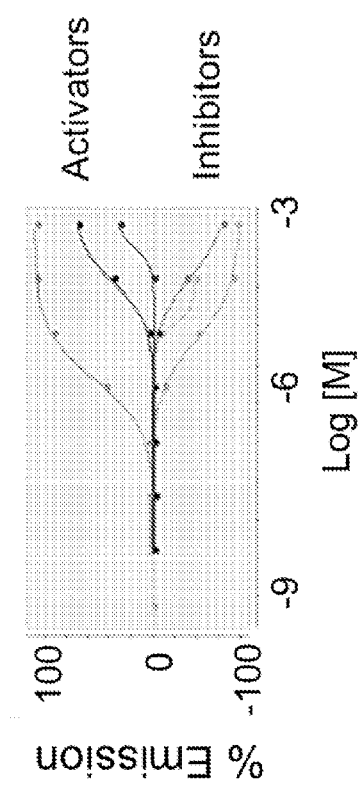

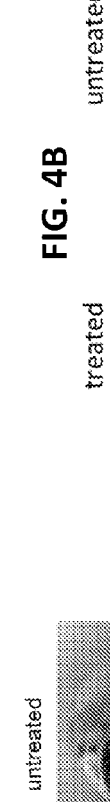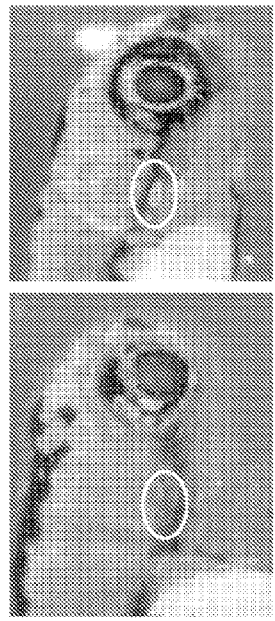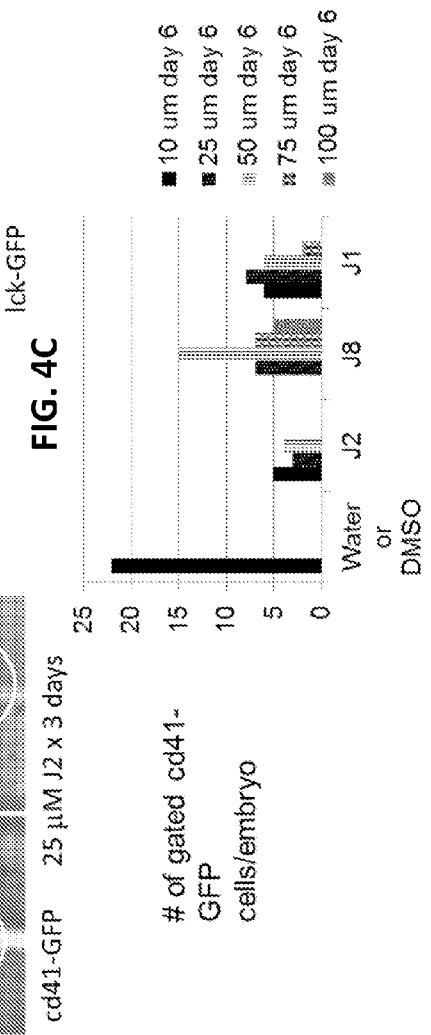
FIG. 4A, FIG. 4B, FIG. 4C: Three structurally related compounds induce runx1-deficient phenotype in zebrafish embryos

FIG. 7
Leukemia Transplantation Model for New Drugs
Leukemia cells from *Cbfb-MYH11* KI mice → Transplant into congenic recipient mice
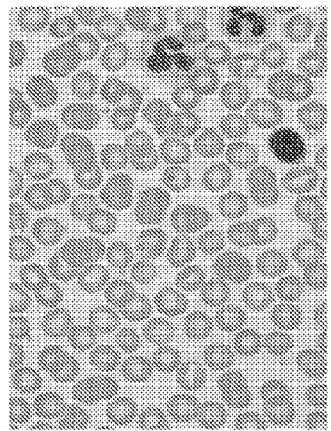
J2 reduces leukemic cell burden
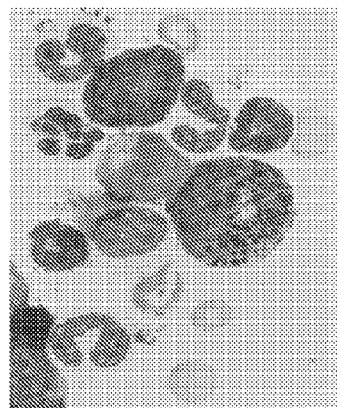
Vehicle alone results in higher leukemic cell burden Reduced leukemic cell burden in mice treated with compound J2

(Plasma concentrations of J2 in the treated mice were only 100 – 200 nM, More than 10 fold lower than those effective in fish and leukemia cell lines.)

FIG. 10
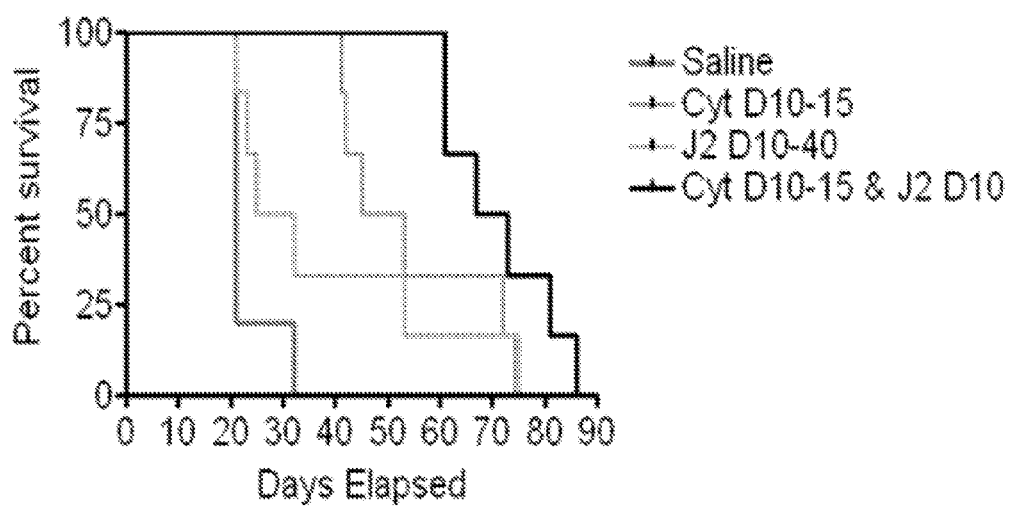
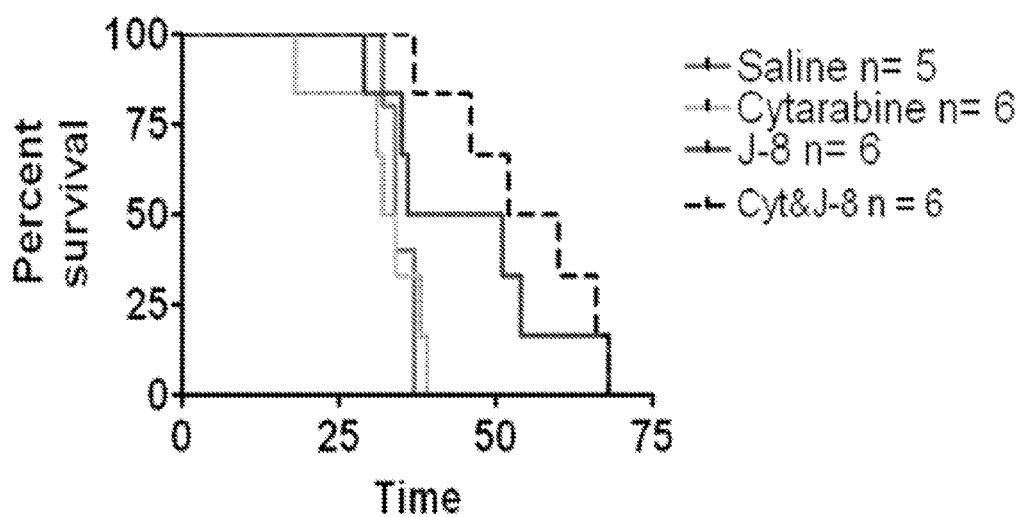

METHODS FOR TREATING LEUKEMIA AND DISORDERS MEDIATED BY CBFβ AND RUNX1 PROTEINS

CROSS REFERENCE TO RELATED APPLICATIONS

This application is the U.S. National Stage of International Application No. PCT/US2012/029169, filed Mar. 15, 2012, which was published in English under PCT Article 21(2), which in turn claims the benefit of U.S. Provisional Application No. 61/453,863, filed Mar. 17, 2011. The provisional application is incorporated herein in its entirety.

BACKGROUND

Leukemia is a cancer of the bone marrow involving the developing white blood cells. Based on disease phenotype, leukemia is divided into myeloid and lymphoid, while based on clinical progression it is also categorized into acute and chronic. Approximately 12,330 new cases of acute myeloid leukemia (AML) and 5,330 new cases of acute lymphoid leukemia (ALL) will be diagnosed in the U.S. in 2010 (according to the Leukemia and Lymphoma Society). Leukemia is often associated with specific, recurrent chromosome translocations and inversions that generate fusion genes, which play critical roles in leukemogenesis.

The Core Binding Factor (CBF) subgroup of leukemia contains CBF fusion genes which have been shown to play critical roles in leukemia development. The CBF family is composed of four proteins, the three a subunits, RUNX1 (AML1, Cbfa2), RUNX2 (Cbfa1), and RUNX3 (Cbfa3), and the single β subunit, CBFβ. CBF leukemias contain chromosome abnormalities affecting CBFβ and RUNX1, which account for approximately 20-30% of all acute myeloid leukemia (AML). Using current state-of-the-art therapy, the 5-year survival rate for CBF leukemias is only around 50%.

SUMMARY

In one embodiment disclosed herein there is provided a method for treating core binding factor (CBF) leukemia in a subject, comprising administering to a subject having CBF leukemia a therapeutically effective amount of a compound, or a pharmaceutically acceptable salt or ester thereof, that inhibits CBFβ and RUNX1 binding in the subject, thereby treating the CBF leukemia.

In a further embodiment, there is disclosed a method for treating core binding factor (CBF) leukemia in a subject, comprising administering to a subject having CBF leukemia a therapeutically effective amount of a compound, or a pharmaceutically acceptable salt or ester thereof, selected from:

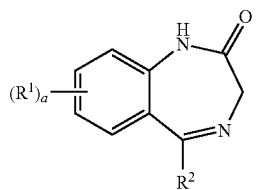

Formula I wherein each $R^1$ is individually selected from halogen, alkyl, aryl, heteroaryl, or alkoxy; $R^2$ is selected from aryl or heteroaryl; and a is 0 to 4;

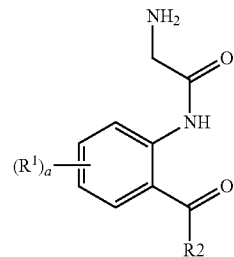

Formula II wherein each $R^1$ is individually selected from halogen, alkyl, aryl, heteroaryl, or alkoxy; $R^2$ is selected from aryl or heteroaryl; and a is 0 to 4; or

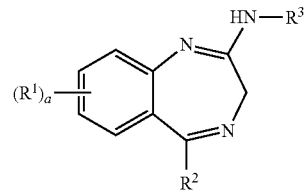

Formula III wherein each $R^1$ is individually selected from halogen, alkyl, aryl, heteroaryl, or alkoxy; $R^2$ is selected from aryl or heteroaryl; $R^3$ is alkyl or aryl; and a is 0 to 4.

In an additional embodiment disclosed herein, there is provided a method for treating a RUNX gene-mediated disorder in a subject, comprising administering to a subject having a RUNX gene-mediated disorder a therapeutically effective amount of a compound, or a pharmaceutically acceptable salt or ester thereof, that inhibits CBFβ and RUNX binding in the subject, thereby treating the CBF leukemia.

According to a further embodiment disclosed herein, there is provided a method for inhibiting interaction between CBFβ and RUNX1 in a cell, comprising contacting the cell with a compound of formulae I-III.

A further embodiment disclosed herein is directed to a pharmaceutical composition that includes (i) at least one compound of formulae I-III and (ii) a chemotherapeutic agent.

An additional embodiment disclosed herein is a method for treating leukemia or another hematopoietic neoplasm in a subject, comprising administering to a subject having leukemia or another hematopoietic neoplasm a therapeutically effective amount of a compound, or a pharmaceutically acceptable salt or ester thereof, selected from:

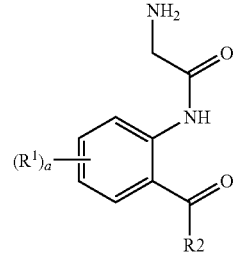

Formula II wherein each $R^1$ is individually selected from halogen, alkyl, aryl, heteroaryl, or alkoxy; $R^2$ is selected from aryl or heteroaryl; and a is 0 to 4; or

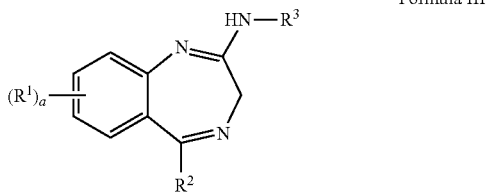

Formula III wherein each $R^1$ is individually selected from halogen, alkyl, aryl, heteroaryl, or alkoxy; $R^2$ is selected from aryl or heteroaryl; $R^3$ is alkyl or aryl; and a is 0 to 4.

Also disclosed herein is a method comprising selecting a subject having CBF leukemia, and administering of at least one of the agents described above to the subject, thereby treating the CBF leukemia.

A further embodiment disclosed herein involves the use of at least one of the agents described above in the manufacture of a medicament(s) for treating CBF leukemia in a subject.

The foregoing will become more apparent from the following detailed description, which proceeds with reference to the accompanying figures.

BRIEF DESCRIPTION OF THE DRAWINGS

FIG. 3 is a schematic representation of a high-throughput screen assay for inhibitors of RUNX1-CBFβ interaction.

FIG. 4 shows the results of compound testing in zebrafish embryos. Compound J1 is MLS000766105, compound J2 is Ro5-3335, and compound J8 is Ro24-7429. These three compounds reduce definitive hematopoiesis in zebrafish embryos.

FIG. 4A is a micrograph of cd41-GFP (platelet) transgenic embryos treated with compound J2.

FIG. 4B is a micrograph of lck-GFP (T cells) transgenic embryos treated with J2.

FIG. 4C is a graph showing reduced numbers of cd41-GFP cells in embryos treated with J1, J2, and J8.

FIG. 7 is a schematic representation of a leukemia transplantation murine model.

FIG. 10 are graphs depicting the survival of leukemic mice treated with candidate compounds. In these two graphs, control mice were given saline and Cyt mice were given cytarabine on days 10-15 after injecting CBF leukemia cells. J2 (Ro5-3335) or J-8 (Ro24-7429) was given on days 10-40 at 300 mg/kg/p.o. The data showed synergy between cytarabine and Ro5-3335. For unknown reasons cytarabine treatment alone failed to extend survival of the leukemic mice in the second experiment, while it's combination with J8 (Ro24-7429) showed a trend of synergy.

DETAILED DESCRIPTION

Figure 1:
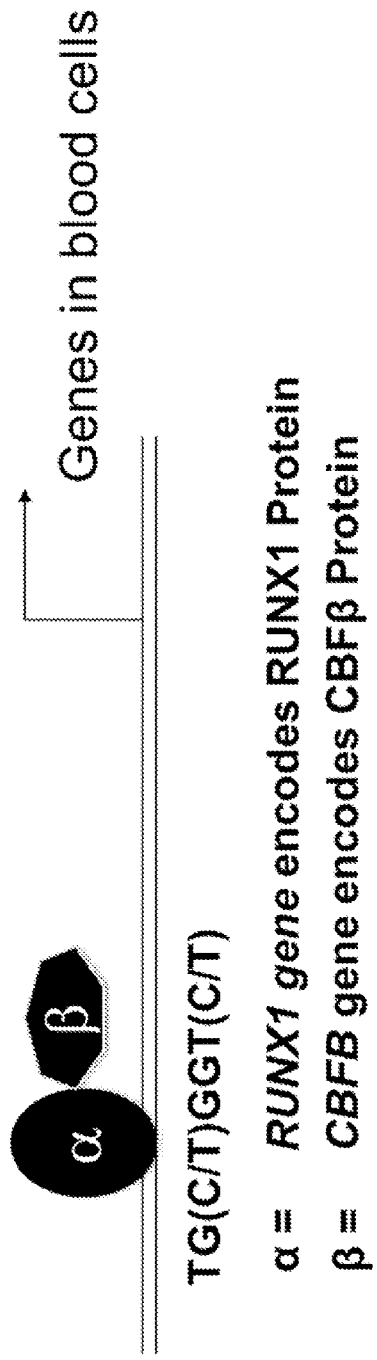
FIG. 1 is a schematic representation of the formation of a DNA-binding, heterodimeric complex by RUNX1 and CBFβ.

The following explanations of terms and methods are provided to better describe the present compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "alkoxy" refers to a group of the formula —OR, wherein R is an organic group such as an alkyl group, optionally substituted with an alkenyl, alkynyl, aryl, aralkyl, cycloalkyl, halogenated alkyl, or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Alkyl groups may be substituted alkyls wherein one or more hydrogen atoms are substituted with a substituent such as halogen, cycloalkyl, alkoxy, amino, hydroxyl, aryl, or carboxyl. For example, an "alkoxyalkyl" has the structure —ROR, wherein R is an alkyl group.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aryl" refers to any carbon-based aromatic group including, but not limited to, benzyl, naphthyl, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be optionally substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "co-administration" or "co-administering" refers to administration of at least two therapeutic compounds within the same general time period, and does not require administration at the same exact moment in time (although co-administration is inclusive of administering at the same exact moment in time). Thus, co-administration may be on the same day or on different days, or in the same week or in different weeks. The therapeutic compounds disclosed herein may be included in the same composition or they may each individually be included in separate compositions. In certain embodiments, the two compounds may be administered during a time frame wherein their respective periods of biological activity overlap. Thus, the term includes sequential as well as coextensive administration of two or more compounds.

The term "derivative" refers to a compound or portion of a compound that is derived from or is theoretically derivable from a parent compound.

The term "heteroaryl" refers to a mono- or poly-cyclic (e.g., bi-, or tri-cyclic or more) fused or non-fused, radical or ring system having at least one aromatic ring, having from five to ten ring atoms of which one ring atom is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

"Inhibiting" refers to inhibiting the full development of a disease or condition. "Inhibiting" also refers to any quantitative or qualitative reduction in biological activity or binding, relative to a control.

The term "neoplasm" refers to an abnormal cellular proliferation, which includes benign and malignant tumors, as well as other proliferative disorders.

"Optional" or "optionally" means that the subsequently described event or circumstance can but need not occur, and that the description includes instances where said event or circumstance occurs and instances where it does not.

The term "pharmaceutically acceptable salt or ester" refers to salts or esters prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977). "Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy$C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable agent.

The pharmaceutically acceptable acid and base addition salts as mentioned hereinabove are meant to comprise the therapeutically active non-toxic acid and base addition salt forms which the agents are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The term "prodrug" also is intended to include any covalently bonded carriers that release a disclosed compound or a parent thereof in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. In particular, ester prodrugs are specifically contemplated herein. Similarly, prodrugs include compounds having an amino or sulfhydryl group functionalized with any group that is cleaved to yield the corresponding free amino or free sulfhydryl group. Examples of prodrugs include, without limitation, compounds having a hydroxy, amino and/or sulfhydryl group acylated with an acetate, formate, or benzoate group.

Protected derivatives of the disclosed compounds also are contemplated. The term "protecting group" or "blocking group" refers to any group that when bound to a functional group prevents or diminishes the group's susceptibility to reaction. "Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. The terms "deprotecting," "deprotected," or "deprotect," as used herein, are meant to refer to the process of removing a protecting group from a compound.

The term "subject" includes both human and veterinary subjects.

A "therapeutically effective amount" refers to a quantity of a specified compound sufficient to achieve a desired effect in a subject being treated with that compound. For example, a therapeutically effective amount may be an amount of a compound that is sufficient to inhibit leukemia in at least one cell, or treat leukemia in a subject. In certain embodiments, a therapeutically effective amount either destroys to target leukemia cells or slows or arrests the progression of leukemia in a subject. Ideally, a therapeutically effective amount of a compound is an amount sufficient to inhibit or treat the disease or condition without causing a substantial cytotoxic effect in the subject. The therapeutically effective amount of a compound will be dependent on the subject being treated, the severity of the affliction, and the manner of administration of the therapeutic composition.

"Treatment" refers to a therapeutic intervention that ameliorates a sign (such as an abnormally elevated level of a marker or other diagnostic identifier) or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer, particularly a metastatic cancer. "Preventing" a disease or condition refers to prophylactic administering a composition to an agent who does not exhibit signs of a disease for the purpose of decreasing the risk of developing a pathology or condition, or diminishing the severity of a pathology or condition.

Figure 2:
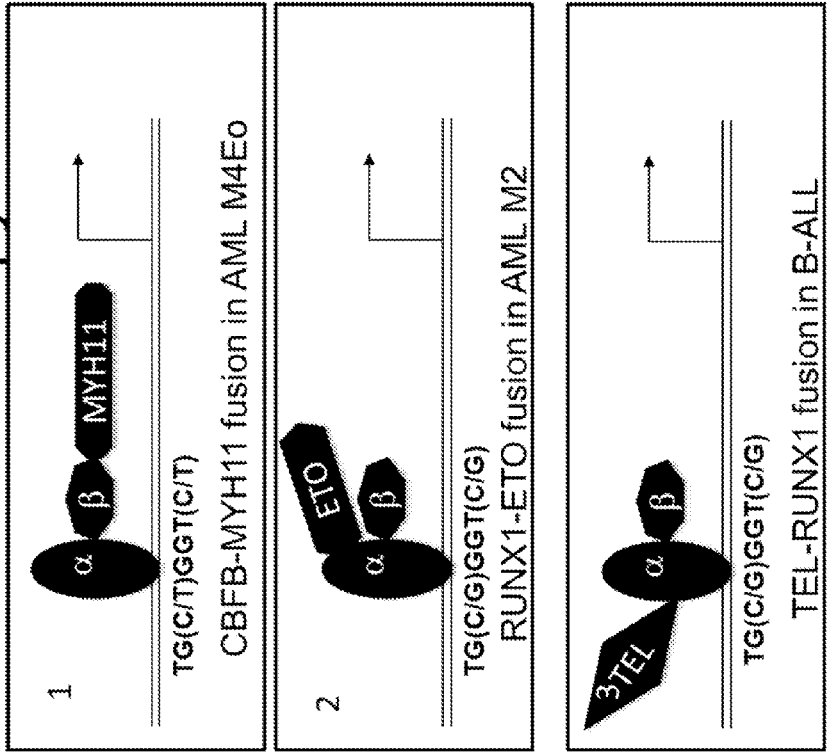
FIG. 2 is a schematic representation of the formation of fusion genes via chromosome translocations in CBF human leukemia.

Leukemia is often associated with specific, recurrent chromosome translocations and inversions that generate fusion genes, which play critical roles in leukemogenesis. Transcription factors RUNX1 and CBFβ form a heterodimer for DNA binding and gene expression regulation (see FIG. 1). They play key roles in normal hematopoiesis. Both genes are involved in leukemogenesis through recurrent chromosome abnormalities (see FIG. 2). A chromosome 16 inversion [(inv)16] that generates a fusion gene between CBFβ and MYH11 (which encodes the smooth muscle myosin heavy chain, SMMHC) is found in virtually all patients with AML subtype M4Eo. A translocation between chromosomes 8 and 21, t(8;21), generates a fusion gene between RUNX1 and ETO, which is found in many patients with AML subtype M2. Finally, a translocation between chromosomes 12 and 21, t(12;21), results in a fusion gene called TEL-RUNX1, which is very common in pediatric ALL. All together the core binding factor (CBF) leukemias, which contain these translocations that affect RUNX1 or CBFβ, account for 20-30% of all AML cases, as well as 20-30% of pediatric ALL cases. Even though CBF leukemias are considered as a "favorable" group of leukemia with better treatment response and prognosis, the long-term survival rate for CBF AML is only 40-50%2. Moreover, current standard care composed of chemotherapy and bone marrow transplantation is frequently associated with significant side effects. Although TEL-RUNX1 pediatric leukemia has a survival rate of >80%, there is significant morbidity associated with the current standard of care.

It has now been discovered that interfering with CBFβ and RUNX1 binding has therapeutic implications for CBF-mediated leukemia. In particular, a library of over 243,000 compounds was screened in a novel in vitro protein-protein interaction assay. Several compounds were identified that inhibited the interaction between CBFβ and RUNX1 at the protein level. These compounds also selectively killed CBF leukemia cells in culture, blocked the RUNX1/CBFβ function in zebrafish embryos, and suppressed leukemia progression in mouse models.

In certain examples, "CBFβ and RUNX1 binding" refers to physical interaction between proteins CBFβ and RUNX1. In certain examples, "CBFβ and RUNX1 interaction" refers to an action that occurs when CBFβ and RUNX1 have effects on each other, which are often required for, or influence, their biological functions.

Examples of active compounds identified herein include:

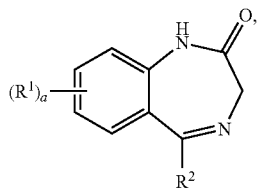

Formula I or pharmaceutically acceptable salts or esters thereof,
wherein each $R^1$ is individually selected from halogen, alkyl, aryl, heteroaryl, or alkoxy; $R^2$ is selected from aryl or heteroaryl; and a is 0 to 4;

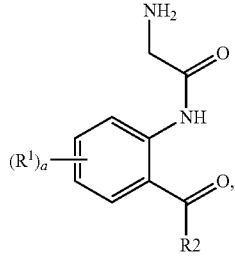

Formula II or a pharmaceutically acceptable salt or ester thereof,
wherein each $R^1$ is individually selected from halogen, alkyl, aryl, heteroaryl, or alkoxy; $R^2$ is selected from aryl or heteroaryl; and a is 0 to 4; or

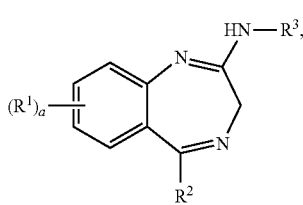

Formula III or a pharmaceutically acceptable salt or ester thereof, wherein each $R^1$ is individually selected from halogen, alkyl, aryl, heteroaryl, or alkoxy; $R^2$ is selected from aryl or heteroaryl; $R^3$ is alkyl or aryl; and a is 0 to 4.

In certain embodiments of formulae I-III, $R^2$ is a heteroaryl, particularly pyrrolyl, and especially pyrrol-2-yl. In certain embodiments of formulae I-III, $R^1$ is a halogen, particularly Cl or F. In certain embodiments of formula III, $R^3$ is a lower alkyl. In certain embodiments of formulae I-III, $R^2$ is a heteroaryl, particularly pyrrolyl, and especially pyrrol-2-yl; and $R^1$ is a halogen, particularly Cl or F. In certain embodiments of formula III, $R^2$ is a heteroaryl, particularly pyrrolyl, and especially pyrrol-2-yl; $R^1$ is a halogen, particularly Cl or F; and $R^3$ is a lower alkyl.

Illustrative compounds include benzodiazepines such as 7-chloro-1-methyl-5-(1H-pyrrol-2-yl)-3H-1,4-benzodiazepin-2-one (NSC156594); 7-chloro-N-methyl-5-1(1H-pyrrol-2-yl)-3H-1,4-benzodiazepin-2-amine (Ro24-7429); or 7-chloro-5-(1H-pyrrol-2-yl)-1,3,-dihydro-1,4-benzodiaepin-2-one (Ro5-3335); and aryl-(2-pyrrolyl) ketone compounds such as 2-amino-N-[4-chloro-2-(1H-pyrrole-2-carbonyl)phenyl]acetamide (MLS000766105; also known as 2-glycineamide-5-chlorophenyl-2-pyrryl ketone (GCPK)). These compounds are described, for example, in U.S. Pat. Nos. 5,641,773; 5,164,376; 5,141,735; 5,041,438; 5,036,101; and 3,405,122.

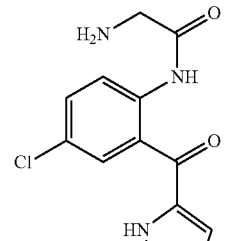

MLS000766105

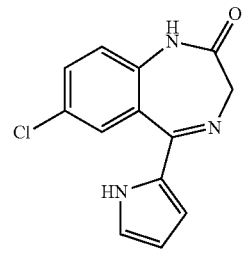

Ro5-3335

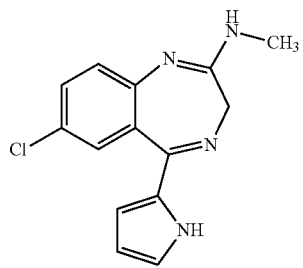

Ro24-7429

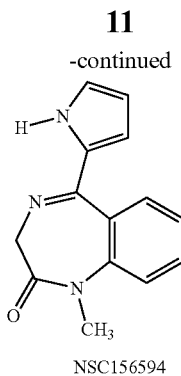

NSC156594

The synthesis of several of these compounds and analogs thereof have been previously described, for example, in U.S. Pat. Nos. 5,641,773; 5,164,376; 5,141,735; 5,041,438; 5,036,101; and 3,405,122.

The amidine derivative (Ro24-7429), a close analogue of Ro5-3335, was reported to exhibit an improved toxicological profile. The original synthetic route for Ro24-7429 involved direct amidination of Ro5-3335, a step that has not yet been achieved in high yield. Therefore, an alternative synthetic route was employed that was developed as described in Scheme 1 (shown below), Maehr H, Zenchoff G, Coffen D L., An alternative synthesis of the Tat-antagonist 7-chloro-N-methyl-5-(1H-pyrrol-2-yl)-3H-1,4-benzodiazepin-2-amine. Bioorg Med Chem 3, 391-395 (1995).

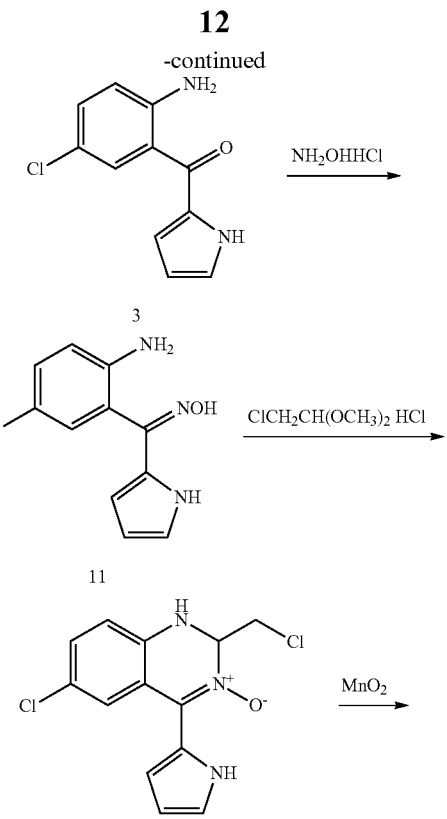

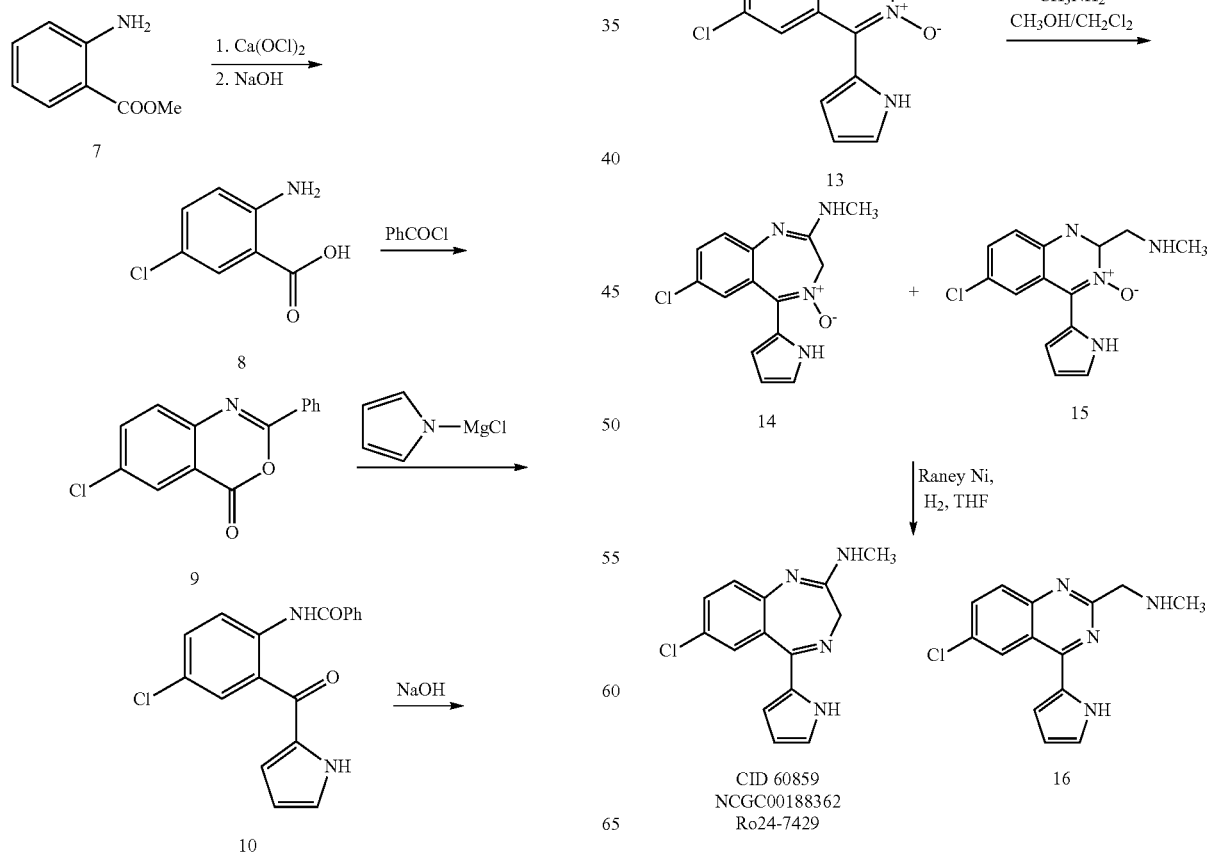

Scheme 1. Synthesis of Ro24-7429

Scheme 2 below shows the initial SAR strategy designed for the ring-opened analogues of Ro5-3335. MLC000766105 was an opened ring version of Ro5-3335 and also found active in the original screening.

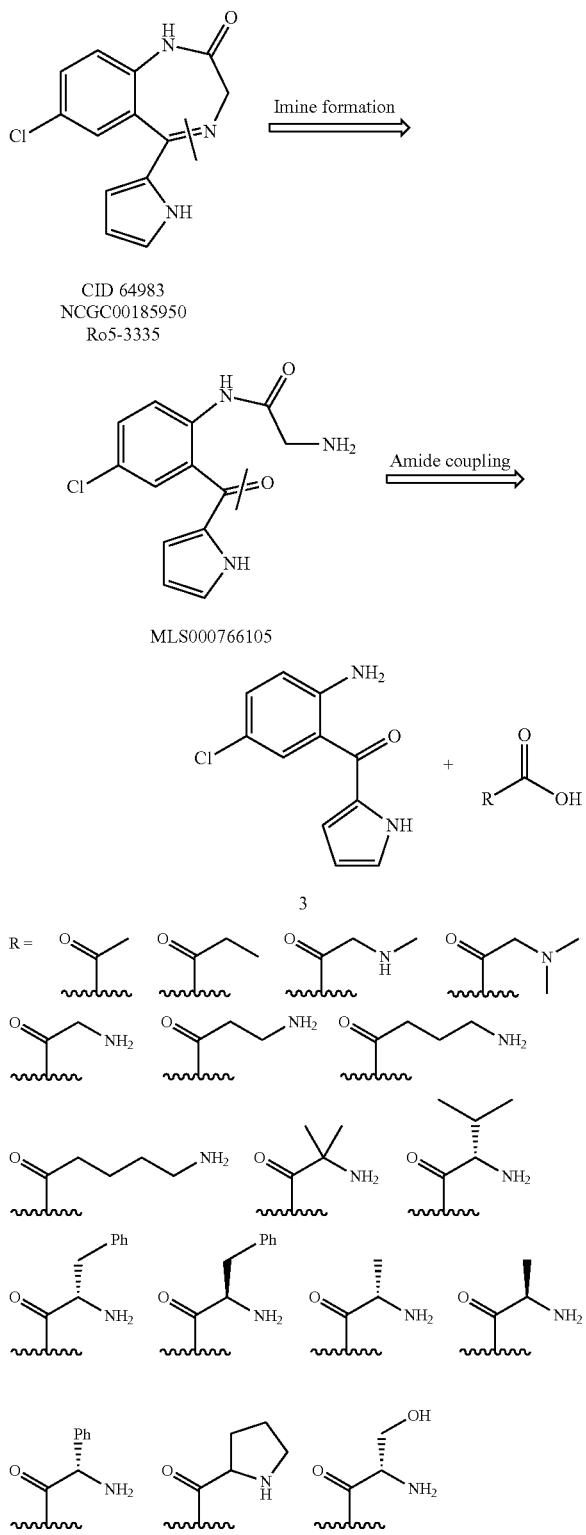

In certain embodiments, the presently disclosed methods are directed to a method for inhibiting CBF leukemia growth, including processes of cellular proliferation, invasiveness, and metastasis in biological systems. Preferably, the method is employed to selectively inhibit CBF leukemia cell proliferation, invasiveness, metastasis, or tumor incidence in living animals, such as mammals. For example, the compounds disclosed herein selectively inhibit CBF leukemia in the sense that the agents exhibit a greater cytotoxicity against CBF leukemia relative to other forms of leukemia.

The killing of cancer cells can occur with less cytotoxicity to normal cells or tissues than is found with conventional cytotoxic therapeutics, preferably without substantial cytotoxicity to normal cells or tissues. For example, the compounds identified herein can induce cytotoxicity in CBF leukemia cells while producing little or substantially no cytotoxicity in normal cells. Thus, unlike conventional cytotoxic anticancer therapeutics, which typically kill all growing cells, the compounds can produce differential cytotoxicity: CBF leukemia cells are selectively killed whereas normal cells are spared. Thus, in another embodiment, there is disclosed a method for inducing differential cytotoxicity in cancer cells relative to normal cells or tissue.

As described above, the compounds disclosed herein are particularly effective for treating CBF leukemia. In one embodiment, the compound may be used for treating AML mediated by a CBFβ-MYH11 fusion gene. In another embodiment, the compound may be used for treating AML mediated by a RUNX1-ETO fusion gene. In a further embodiment, the compound may be used for treating ALL mediated by a TEL-RUNX1 fusion gene.

Diagnosis of hematopoietic malignancies by complete blood counts, bone marrow aspiration and biopsy, immunophenotyping and other tests are known and routinely used. In addition to high resolution chromosome banding and advanced chromosomal imagining technologies, chromosome aberrations in suspected cases in suspected cases of hematopoietic malignancies can be determined through cytogenetic analysis such as fluorescence in situ hybridization (FISH), karyotyping, spectral karyotyping (SKY), multiplex FISH (M-FISH), comparative genomic hybridization (CGH), singly nucleotide polymorphism arrays and other diagnostic and analysis tests known and used by those skilled in the art. The most commonly used laboratory procedure to determine if a patient has CBF leukemia is RT-PCR, which is used routinely in the hematology/oncology field. RNA from patient leukemia cells are used for reverse transcription to generate cDNA, which can then be used for PCR reactions with primers flanking the breakpoints in inv(16), t(8;21), and t(12;21), which generate the fusion genes CBFB-MYH11, AML1-ETO, and TEL-AML1, respectively (van Dongen, J. J., Macintyre, E. A., Gabert, J. A., Delabesse, E., Rossi, V., Saglio, G., Gottardi, E., Rambaldi, A., Dotti, G., Griesinger, F., et al. Leukemia 13: 1901-1928, 1999).

The compounds disclosed herein may also be co-administered with another chemotherapeutic agent. The chemotherapeutic agents may be other agents suitable for treating leukemia. Illustrative chemotherapeutic agents include cytarabine (also known as cytosine arabinoside), an anthracycline (e.g., daunorubicin, idarubicin), all-trans-retinoic acid (ATRA), histamine dihydrochloride, interleukin-2, getuzumab ozogamicin, clofarabine, etoposide, mitoxantrone, topotecan, fludarabine, L-asparaginase, vincristine, 6-mercaptopurine, methotrexate, dexamethasone, bortezomib, and combinations thereof. The compounds disclosed herein may be administered in connection with stem cell transplantation (allogenic or hematopoietic).

In a further embodiment, the compounds disclosed herein may also be co-administered with a kinase inhibitor. Illustrative kinase inhibitors include afatinib, alvocidib, axitinib, bosutinib, cediranib, crizotinib, dasatinib, E7080, eroltinib, everolimus, gefitinib, imatinib, lapatinib, lestaurtinib, masitinib, mubritinib, neratinib, nilotinib, pazopanib, PLX4032, regorafenib, ruxolitinib, semaxanib, sorafenib, sunitinib, temsirolimus, toceranib, tofacitinib, vandetanib, vatalanib, and combinations thereof.

In addition, RUNX genes have been implicated in many other disorders, such as bone diseases, platelet disorders, and solid tumors. Therefore, the compounds disclosed herein may exert therapeutic effects on RUNX gene-mediated disorders. Illustrative RUNX gene-mediated disorders include bone diseases (e.g., osteoporosis, cleidocranial dysplasia, invertebral disc degeneration) (Khalid et al, Modulation of Runx2 activity by estrogen receptor-alpha: implications for osteoporosis and breast cancer. Endocrinology. 2008 December; 149(12):5984-95. Epub 2008 Aug. 28; Song et al., Haploinsufficiency of CBFA2 causes familial thrombocytopenia with propensity to develop acute myelogenous leukemia. Nat Genet. 1999 October; 23(2):166-75; Sato et al. The distinct role of the Runx proteins in chondrocyte differentiation and intervertebral disc degeneration: findings in murine models and in human disease. Arthritis Rheum. 2008 September; 58(9):2764-75); platelet disorders; and solid tumors (e.g., lymphoma, breast, osteosarcoma) (Blyth et al., Runx1 promotes B-cell survival and lymphoma development. Blood Cells Mol Dis. 2009 July-August; 43(1):12-9; Mendoza-Villanueva et al. The Runx transcriptional co-activator, CBFbeta, is essential for invasion of breast cancer cells. Mol Cancer. 2010 Jun. 30; 9:171; Pratap et al. Bone. 2010 Jun. 1).

The compounds identified herein may be included in a pharmaceutical composition that includes at least one pharmaceutically acceptable additive such as a carrier, thickener, diluent, buffer, preservative, surface active agent and the like in addition to the agent. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The compounds disclosed herein can be administered to subjects by a variety of mucosal administration modes, including by oral, rectal, intranasal, intrapulmonary, or transdermal delivery, or by topical delivery to other surfaces. Optionally, the compounds can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compounds can be administered ex vivo by direct exposure to cells, tissues or organs originating from a subject.

To formulate the pharmaceutical compositions, the compounds can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compounds can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compounds can be combined with the base or vehicle according to a variety of methods, and release of the compounds can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compounds can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compounds can be delivered to a subject in a manner consistent with conventional methodologies associated with management of the disorder for which treatment or prevention is sought. In accordance with the disclosure herein, a prophylactically or therapeutically effective amount of the compound is administered to a subject in need of such treatment for a time and under conditions sufficient to prevent, inhibit, and/or ameliorate a selected disease or condition or one or more symptom(s) thereof.

The administration of the compounds can be for either prophylactic or therapeutic purpose. When provided prophylactically, the compounds are provided in advance of any symptom. The prophylactic administration of the compounds serves to prevent or ameliorate any subsequent disease process. When provided therapeutically, the compound is provided at (or shortly after) the onset of a symptom of disease or infection.

For prophylactic and therapeutic purposes, the compounds can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the compounds will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the compound are outweighed in clinical terms by therapeutically beneficial effects. A non-limiting range for a therapeutically effective amount of a compound within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

Example 1

High-Throughput Screen Assay for Blocking the Interaction Between RUNX1 and CBFβ

An Amplified Luminescence Proximity Homogenous Assay (ALPHA) Screen format (PerkinElmer) was used to develop an assay for identifying compounds that affect RUNX1-CBFβ binding (see FIG. 3) optimized for high throughput screening (HTS). The full length biotinylated RUNX1, histagged CBFβ and untagged CBFβ proteins were purchased from Genecopoeia (Germantown, Md.) that were prepared in a wheat germ extract cell-free protein translation system. All three proteins were purified using an affinity column and FPLC chromatography. The assay buffer was comprised of 25 mM HEPES (pH 7.4), 110 mM KCl, 2 mM $MgCl_2$, 10 mM NaCl, 5 mM DTT, and 0.01% Tween-20. The AlphaScreen assay platform (PerkinElmer) was applied for the measurement of interaction of Runx1 protein with the CBFb protein. The assay was developed in 384-well plate format and optimized in 1536-well plate format for high throughput screening. Briefly, in a 1536-well black plate, 3 ul/well of biotinylated RUNX1 (30 nM) and histagged CBFβ were incubated with the 23 nl of compound DMSO solution for 30 minutes at the room temperature. Then, 1 µl/well of both AlphaScreen beads, nickel-chelate acceptor beads and streptavidin coated donor beads, was added to the assay plate and incubated for 60 minutes at room temperature. The assay plate was measured in an AlphaScreen mode using an Envision plate reader (Perkin Elmer, Waltham, Mass.). The compounds that reduced the AlphaScreen signal by disrupting the binding between RUNX1 and CBFβ proteins were selected as the active compounds.

Synthesized, tagged RUNX1 and CBFβ were used in the assay and a total of over 240,000 compounds at 7 concentrations each were screened with this assay. The HTS hits were selected using the criteria of IC50<30 µM and maximal inhibition >70%, which resulted in the identification of 458 putative inhibitors. Confirmatory ALPHA and HTRF (homogeneous time resolved fluorescence) assays were performed to prioritize compounds for their ability to inhibit RUNX1-CBFβ interaction.

Example 2

Blockage of Zebrafish Embryonic Hematopoieses as a Readout for RUNX1/CBFβ Interaction Candidate compounds were tested in a zebrafish model to determine if they specifically block RUNX1-CBFβ interaction. RUNX1 and CBFβ are required for definitive hematopoiesis during embryogenesis, since RUNX1 and CBFβ knockout mouse embryos are devoid of definitive blood cells. Thus, inhibitors of RUNX1 and CBFβ should also be able to block definitive hematopoiesis as well. Standard protocols were used to breed and raise embryos from the cd41-GFP transgenic fish in which GFP marks hematopoietic stem cells, in addition to thrombocytes during embryogenesis, and from the lck-GFP transgenic fish in which GFP marks the T lineage cells. (See Westerfield M, ed

*The Zebrafish Book, A guide for the laboratory use of zebrafish (Danio rerio).* Edition 3 ed. Eugene, Oreg.: University of Oregon Press; 1995; Lin et al. Analysis of thrombocyte development in CD41-GFP transgenic zebrafish. *Blood.* Dec. 1, 2005; 106(12):3803-3810; Bertrand et al. CD41+ cmyb+ precursors colonize the zebrafish pronephros by a novel migration route to initiate adult hematopoiesis. *Development.* May 2008; 135(10):1853-1862; Bertrand et al. Definitive hematopoiesis initiates through a committed erythromyeloid progenitor in the zebrafish embryo. *Development.* December 2007; 134(23):4147-4156; Kissa et al. Live imaging of emerging hematopoietic stem cells and early thymus colonization. *Blood.* Feb. 1, 2008; 111(3): 1147-1156; Langenau et al. In vivo tracking of T cell development, ablation, and engraftment in transgenic zebrafish. *Proc Natl Acad Sci USA.* May 11, 2004; 101(19): 7369-7374). Compounds were added to the water at 24 hours post fertilization and the final DMSO concentrations were less than 0.1%. The embryos were then observed, photographed, and videotaped with a Leica MZ16F dissecting scope, equipped with a Leica DC500 camera and a BioVision Vision-Mac™ video system. The numbers of GFP+ cells in each embryo were counted manually.

As shown in FIG. 4, using transgenic zebrafish embryos that express GFP from cd41 or lck promoters, which are active in thrombocytes/platelets and T cells respectively, three compounds (MLS000766105, Ro5-3335, and Ro24-7429, which are J1, J2, and J8, respectively in FIG. 4) were identified that led to significant reduction of definitive hematopoiesis. Compound treatments did not generate gross toxicity during 5 days of fish embryo development.

Example 3

Selective Cytotoxicity for CBF Leukemia Cell Lines

Cell lines including HeLa, HL-60, Kasumi-1, Kasumi-6, ME-1, RS4 and REH were obtained from American Type Culture Collection (ATCC, Manassas, Va.). Cells in suspension at a density of 100,000 cells/ml were grown in a T175 flask with 20% FBS RPMI-1640 medium except 20% FBS IMDM medium for HL-60 cell line and the medium was renewed every 2-3 days. The cells were centrifuged and resuspended in 10% FBS phenol free OPTI-MEM medium which were seeded at 500 cells/well in 5 uL in 1536-well white solid-bottom plates using a Multidrop Combi dispenser (ThermoFisher Scientific Inc., Waltham, Mass.). The assay plates were incubated at 37° C. with 5% CO2 and 95% humidity for 2 hours prior to compound addition. Subsequently, 23 nL/well compound DMSO solutions or DMSO controls were transferred to the assay plates using a Kalypsys pintool workstation (Kalypsys, San Diego, Calif.). The plates were then incubated at 37° C. with 5% CO2 and 95% humidity for 24 hours followed by an addition of 4 uL/well of ATPlite reagent (PerkinElmer). After a 20 minute incubation, the plates were measured in the luminescence mode using a ViewLux plate reader (Perkinelmer, Waltham, Mass.).

Figure 5:
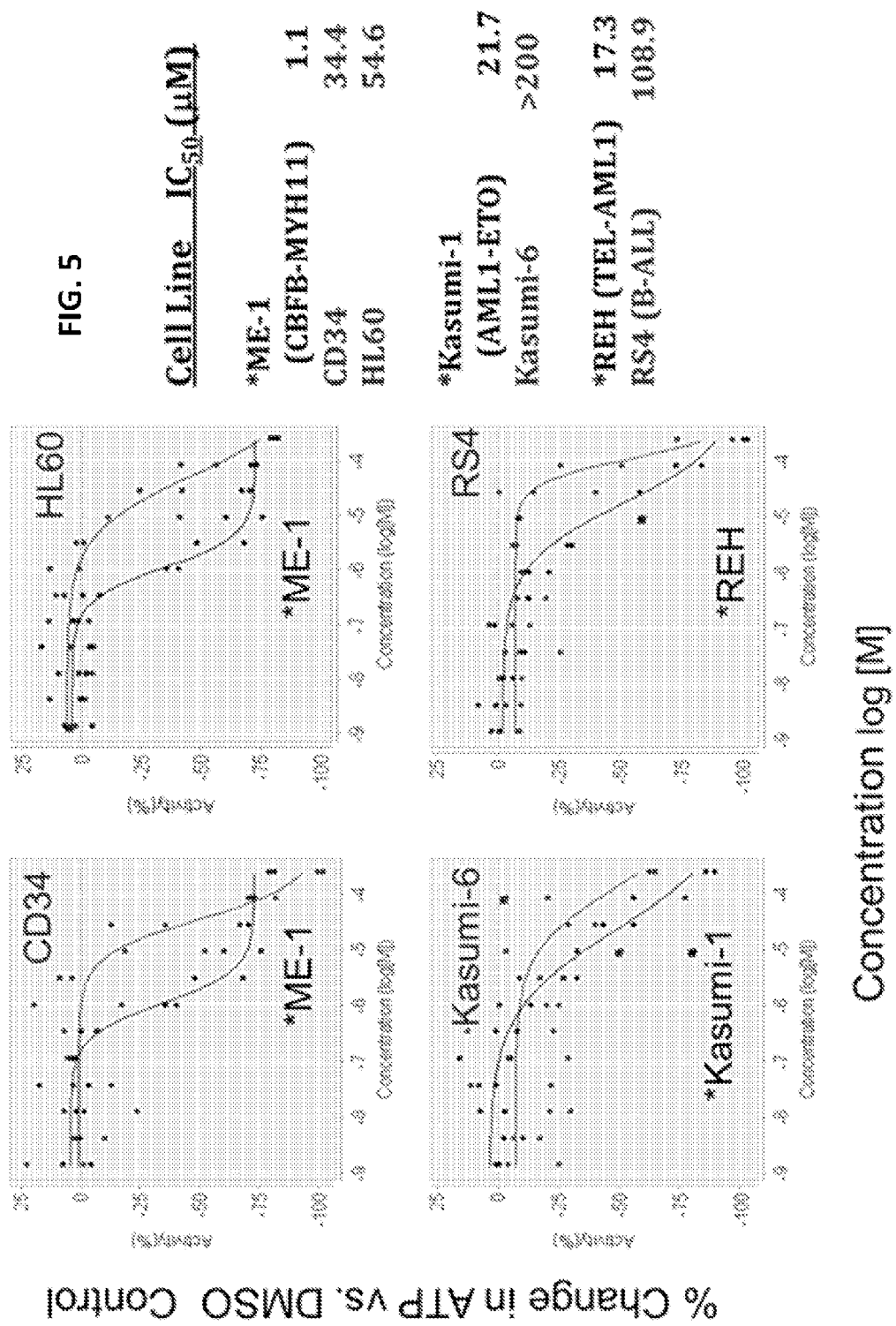
FIG. 5 depicts the results of treating leukemia cells with or without CBF fusion genes with Ro5-3335. The graphs on the left shows % change of ATP contents in ME-1 (black line) and HL-60 (blue line) cells after treatment with Ro5-3335 at the indicated concentrations. ME-1 contains the CBFB-MYH11 fusion gene and HL-60 does not. The table on the right shows IC50 values for the listed cell lines. The cellular ATP content was measured by a luciferase based viability assay with −100% as 100% cell killing.
Figure 6:
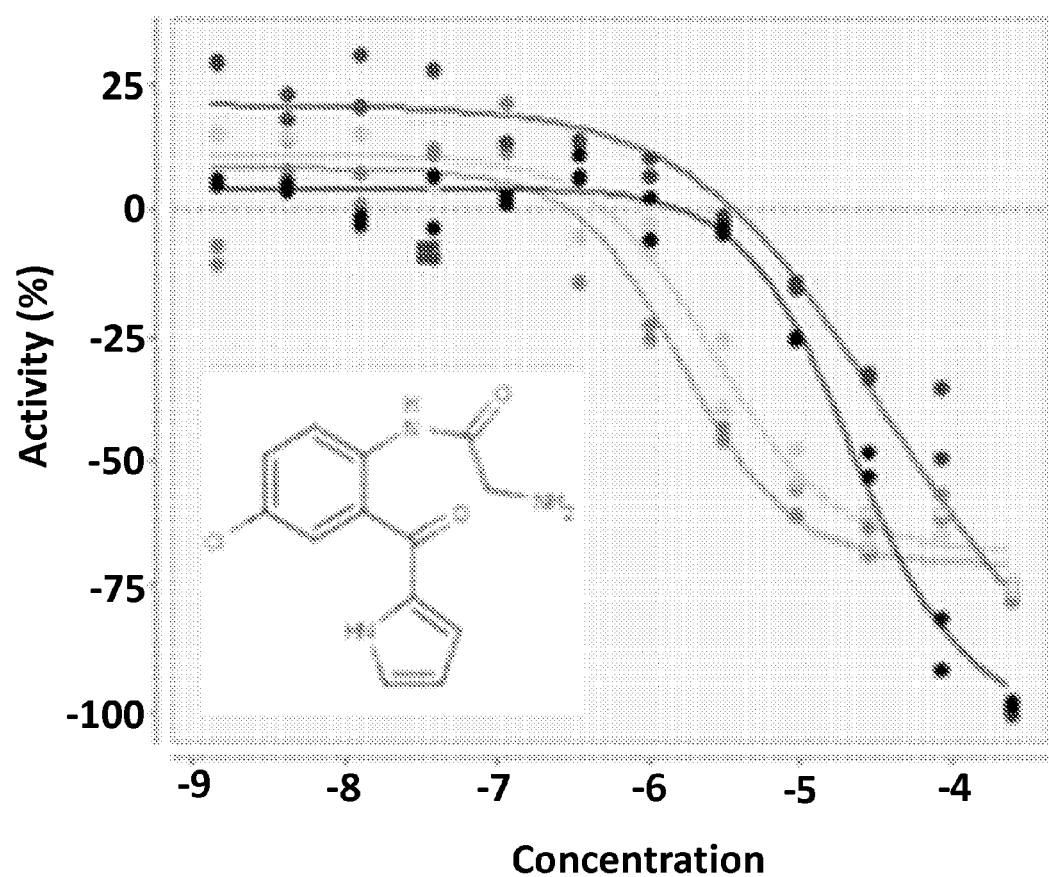
FIG. 6 depicts the results of treating leukemia cells with or without CBF fusion genes with MLS000766105. Grey line; ME-1; Cyan: Kasume-1; Blue: HL-60; Black: HeLa.
Figure 8:
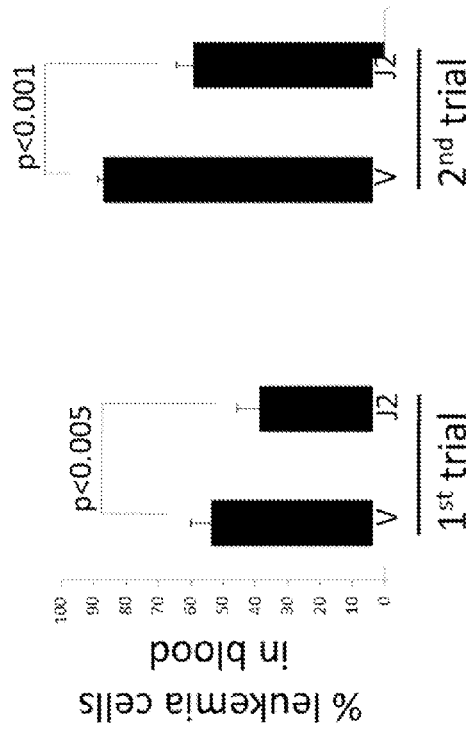
FIG. 8 shows graphs depicting the results of employing an agent disclosed herein (compound J2 is Ro5-3335) in the leukemia transplantation murine model shown in FIG. 7. "V" represents the vehicle alone.
Figure 9:
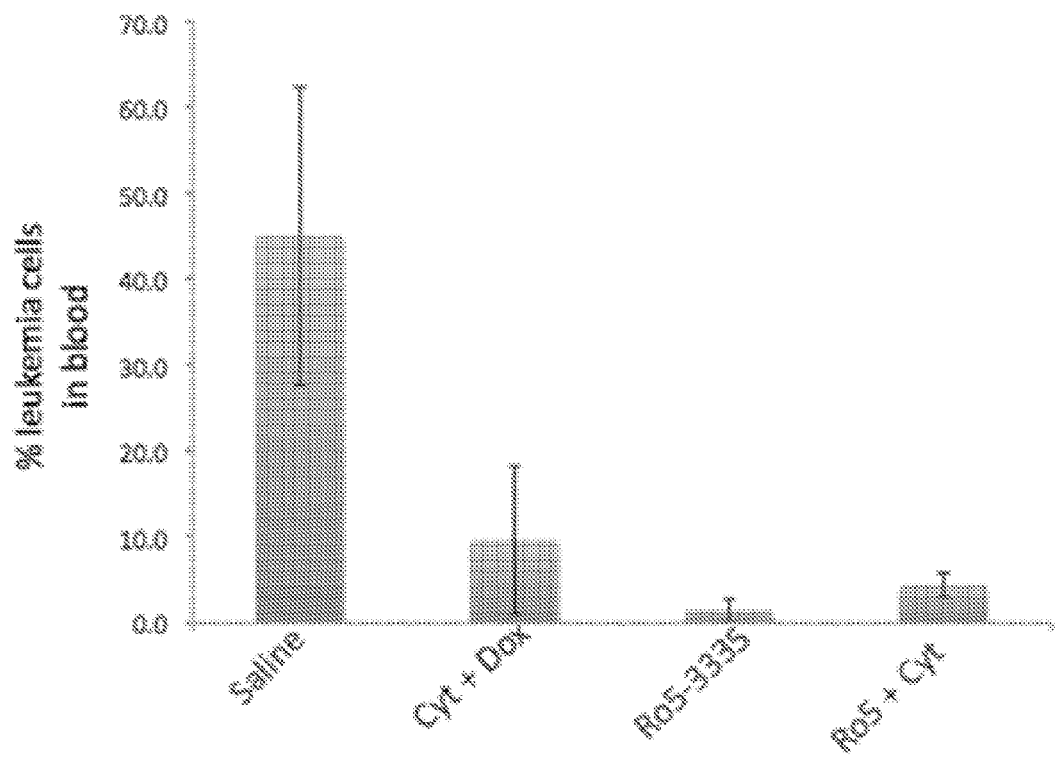
FIG. 9 is a graph demonstrating the reduced leukemia cell burden in mice treated with compound Ro5-3335. Cyt: cytarabine. Dox: doxorubicin. The data were collected 10 days after treatments started. N=6 for each group except for saline, which had 5 mice. Leukemia cell percentages were represented by c-kit+ cells.

The results (see FIGS. 5 and 6) showed that Ro5-3335 and MLS000766105 preferentially killed leukemia cells with CBF fusion genes. As shown in FIGS. 5 and 6, cell killing activities of Ro5-3335 for CBF leukemia cell lines were 6-50 fold more potent than those for leukemia cell lines without CBF fusion genes. In addition, there was selective killing of the CBFB-MYH11 containing ME-1 cells over normal CD34 cells.

Example 4

Leukemia Murine Model

Compound Ro5-3335 was tested in a CBFβ-MYH11 knock-in mouse model that faithfully models human leukemia with this fusion gene. The mouse model is described in Castilla et al, Failure of embryonic hematopoiesis and lethal hemorrhages in mouse embryos heterozygous for a knocked-in leukemia gene CBFB-MYH11. Cell. 1996; 87(4):687-696; Castilla et al., The fusion gene Cbfb-MYH11 blocks myeloid differentiation and predisposes mice to acute myelomonocytic leukemia. Nat. Genet. October 1999; 23[2]:144-146. The CBFB-MYH11 fusion gene in this mouse model initiates leukemia development with high penetrance but variable latency. However, when the leukemia cells are transplanted, the recipient mice develop leukemia with very short, consistent latency and 100% penetrance.

The B6129F1/J mice were used for injection of leukemia cells developed in the Cbfb-MYH11 knock-in mice. The recipient mice were irradiated at 900 rads before the leukemia cells were given through retro-orbital vein injection, typically at around 250,000-500,000 cells/mouse. Ten days after leukemia cell injection, the mice were given the candidate compounds Ro5-3335 and Ro24-7429 in transgenic dough, at 300 mg/kg/day for up to 30 days. Cytarabine was given for 6 consecutive days starting on day 10 after transplantation, at 100 mg/kg/day IP, and doxorubicin was given for 4 consecutive days starting on day 10 after transplantation, at 3 mg/kg/day IP. The mice were followed by daily inspection and bi-weekly analysis of peripheral blood, which was collected by retro-orbital bleeding. Leukemia cells in the peripheral blood were evaluated by FACS analysis and by blood smear observation. Moribund mice were sacrificed and necropsy conducted to ascertain the diagnosis of terminal leukemia.

The data (see FIGS. 7-10) show that Ro5-3335 and Ro24-7429 significantly reduced the leukemia burden in these mice with similar efficacy as standard chemotherapy drugs.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A method for treating core binding factor (CBF) leukemia in a subject, comprising administering to a subject having CBF leukemia a therapeutically effective amount of a compound, or a pharmaceutically acceptable salt or ester thereof, selected from:

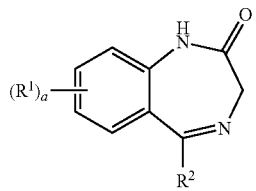

Formula I wherein each R¹ is individually halogen; R² is pyrrolyl; and a is 0 to 4;

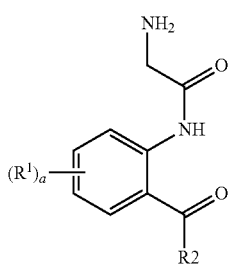

Formula II wherein each R¹ is halogen; R² is pyrrolyl; and a is 0 to 4; or

Formula III wherein each R¹ is halogen; R² is pyrrolyl; R³ is lower alkyl; and a is 0 to 4; or

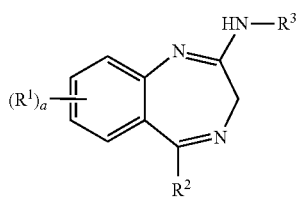

2. The method of claim 1, further comprising co-administering the compound with a chemotherapeutic agent.

3. The method of claim 2, wherein the chemotherapeutic agent is selected from cytarabine, an anthracycline, all-trans-retinoic acid (ATRA), histamine dihydrochloride, interleukin-2, getuzumab ozogamicin, clofarabine, or a combination thereof.

4. The method of claim 1 further comprising co-administering the compound with a kinase inhibitor.

5. The method of claim 1, wherein the compound is selected from:

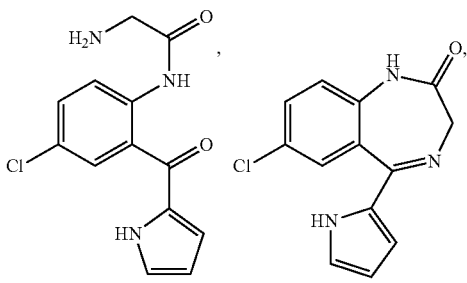

6. The method of claim 1, wherein the compound is:

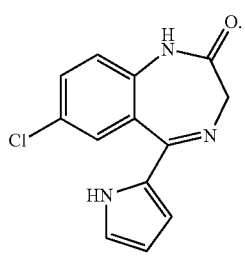 [SMILES: O=C1CN=C(c2ccc[nH]2)c2cc(Cl)ccc2N1]

7. The method of claim 1, wherein the compound is:

8. The method of claim 1, wherein the compound is:

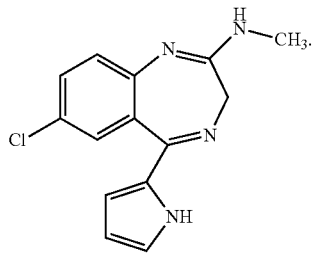 [SMILES: CNC1=Nc2ccc(Cl)cc2C(c2ccc[nH]2)=NC1]

9. The method of claim 1, wherein the compound is:

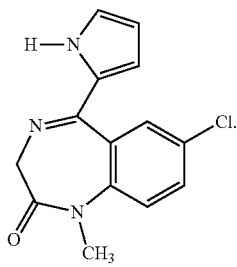 [SMILES: CN1C(=O)CN=C(c2ccc[nH]2)c2cc(Cl)ccc21]

10. The method of claim 1, wherein the CBF leukemia is selected from acute myeloid leukemia mediated by a CBFβ-MYH11 fusion gene, acute myeloid leukemia mediated by a RUNX1-ETO fusion gene, or acute lymphoid leukemia mediated by a TEL-RUNX1 fusion gene.

11. A method for inhibiting interaction between CBFβ and RUNX1 in a cell, comprising contacting the cell with a compound, or a pharmaceutically acceptable salt or ester thereof, selected from:

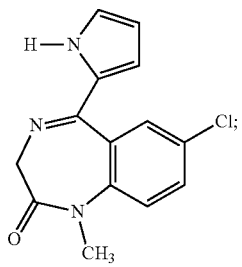 [SMILES: CN1C(=O)CN=C(c2ccc[nH]2)c2cc(Cl)ccc21]

12. The method of claim 11, wherein inhibiting interaction between CBFβ and RUNX1 in a cell inhibits formation of at least one of the following: CBFβ-MYH11 fusion gene, RUNX1-ETO fusion gene, or TEL-RUNX1 fusion gene.

13. A pharmaceutical composition comprising:
(i) at least one compound, or a pharmaceutically acceptable salt or ester thereof, selected from:

and
(ii) at least one chemotherapeutic agent suitable for treating leukemia, or a pharmaceutically acceptable salt thereof.

* * * * *